United States Patent
Khan et al.

(10) Patent No.: US 11,891,312 B1
(45) Date of Patent: Feb. 6, 2024

(54) MAGNETIC HYDROCHAR SYNTHESIZED FROM MICROALGAL BIOMASS

(71) Applicant: KING SAUD UNIVERSITY, Riyadh (SA)

(72) Inventors: Moonis Ali Khan, Riyadh (SA); Byong-Hun Jeon, Riyadh (SA); Ayoub Abdullah Alqadami, Riyadh (SA); El-Sayeed Salama, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 18/119,996

(22) Filed: Mar. 10, 2023

(51) Int. Cl.
| | |
|---|---|
| *C02F 1/28* | (2023.01) |
| *A61K 8/9711* | (2017.01) |
| *B01J 20/02* | (2006.01) |
| *B01J 20/20* | (2006.01) |
| *B01J 20/28* | (2006.01) |
| *B01J 20/30* | (2006.01) |
| *C02F 1/62* | (2023.01) |
| *C02F 1/68* | (2023.01) |
| *C02F 101/20* | (2006.01) |

(52) U.S. Cl.
CPC .......... *C02F 1/283* (2013.01); *A61K 8/9711* (2017.08); *B01J 20/0229* (2013.01); *B01J 20/20* (2013.01); *B01J 20/28009* (2013.01); *B01J 20/3078* (2013.01); *C02F 1/62* (2013.01); *B01J 20/3085* (2013.01); *B01J 2220/4843* (2013.01); *C02F 1/683* (2013.01); *C02F 2101/20* (2013.01)

(58) Field of Classification Search
None
See application file for complete search history.

(56) References Cited

U.S. PATENT DOCUMENTS 10,557,098 B1   2/2020   Khan

FOREIGN PATENT DOCUMENTS

| CN | 101642699 A |   | 2/2010  |           |
|----|-------------|---|---------|-----------|
| CN | 109317100 A | * | 2/2019  | B01J 20/20 |
| CN | 109395700 A |   | 3/2019  |           |
| CN | 110252242 A |   | 9/2019  |           |
| CN | 10586046 A  |   | 12/2019 |           |
| CN | 110586035 A |   | 12/2019 |           |

(Continued)

OTHER PUBLICATIONS

Xue et al. (Chemical Engineering Journal, 2012, vol. 200-202, 673-680). (Year: 2012).*

(Continued)

*Primary Examiner* — Clare M Perrin
(74) *Attorney, Agent, or Firm* — Nath, Goldberg & Meyer; Richard C. Litman

(57) ABSTRACT

Magnetized hydrochar for the adsorption of cadmium and a method of synthesizing magnetized hydrochar from microalgal biomass are provided. The magnetized hydrochar may be synthesized by subjecting a microalgal biomass to a hydrothermal carbonization (HTC) reaction to produce hydrochar, chemically activating the hydrochar with $H_2O_2$, and magnetizing the activated hydrochar through coprecipitation. The microalgal biomass may be selected from *Chlorella vulgaris* FR751187 or *Scenedesmus obliquus* GU732418. The resulting mHC may be used to adsorb cadmium ions from an aqueous environment, including but not limited to waste effluent.

10 Claims, 12 Drawing Sheets

(56) References Cited

FOREIGN PATENT DOCUMENTS

| CN | 110681350 A | 1/2020 |
|---|---|---|
| CN | 110756167 A | 2/2020 |
| CN | 110813230 A | 2/2020 |
| CN | 110833815 A | 2/2020 |
| WO | 2016072932 A1 | 5/2016 |

OTHER PUBLICATIONS

Joo et al. (Envion Sci Pollut Res, 2021, 28, 25390-25399). (Year: 2021).*

Monteiro et al. (World J Microbiol Biotechnol, 2009, 25, 1573-1578). (Year: 2009).*

Machine translation of CN 109317100A, pp. 1-8, 2019. (Year: 2019).*

Wang et al. (Journal of Hazardous Materials, 2020, 395, 122658). (Year: 2020).*

Son et al. (Science of the Total Environment, 2018, 615, 161-168). (Year: 2018).*

Son et al. (Bioresource Technology, 2018, 259, 381-387). (Year: 2018).*

Singh et al. (Science of the Total Environment, 2021, 774, 145676). (Year: 2021).*

Chen et al. (Ecotoxicology and Environmental Safety, 2018, 164, 440-447). (Year: 2018).*

Nguyen et al. (Bioresource Technology, 2022, 346, 126351). (Year: 2022).*

Lalhmunsiama et al. (Journal of the Taiwan Institute of Chemical Engineers, 2017, 71, 206-213). (Year: 2017).*

Niazi, N.K. et al., "Chapter 7—Removal and Recovery of Metals by Biosorbents and Biochars Derived From Biowastes," Environmental Materials and Waste Resource Recovery and Pollution Prevention, 2016, pp. 149-177.

Li, X. et al., "Preparation and application of magnetic biochar in water treatment: A critical review," Science of the Total Environment, vol. 711, Apr. 1, 2020.

* cited by examiner

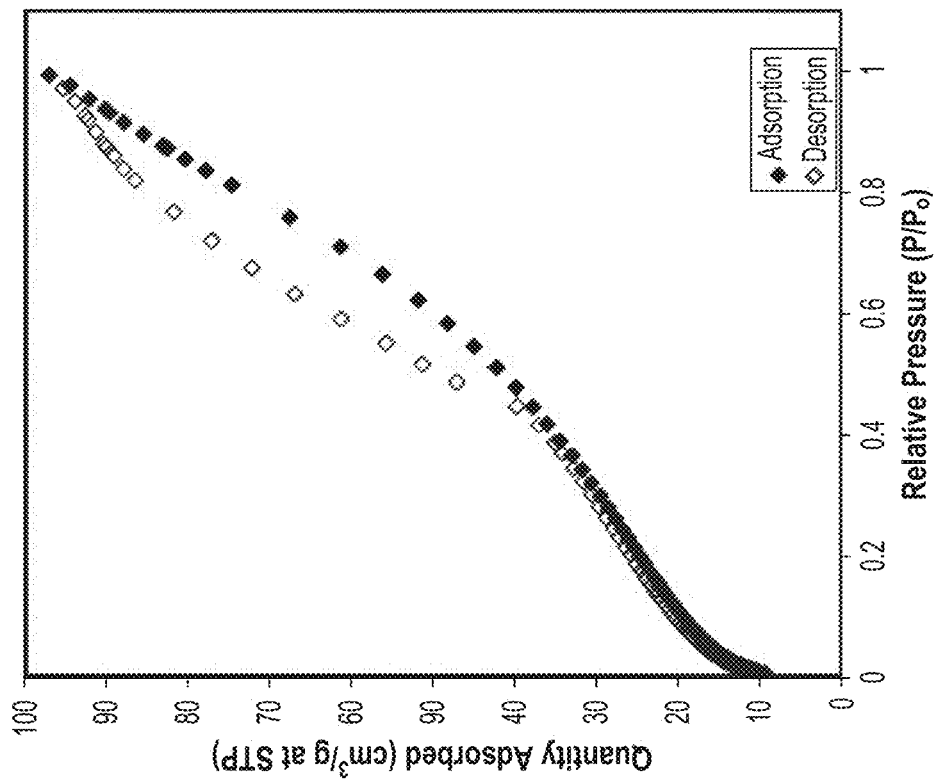
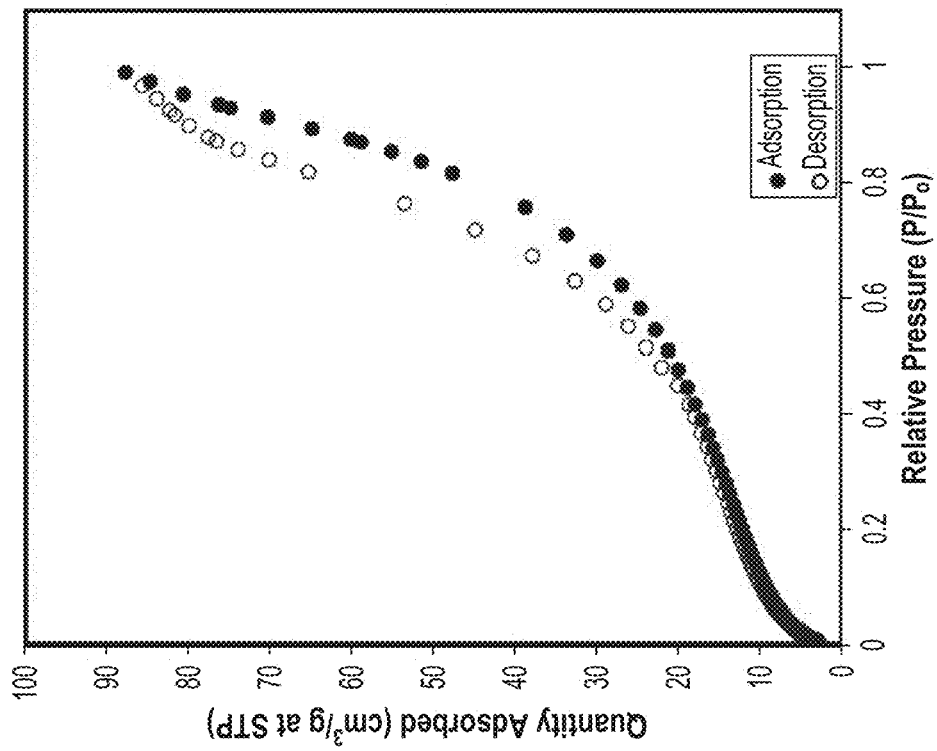
FIG. 1A
FIG. 1B

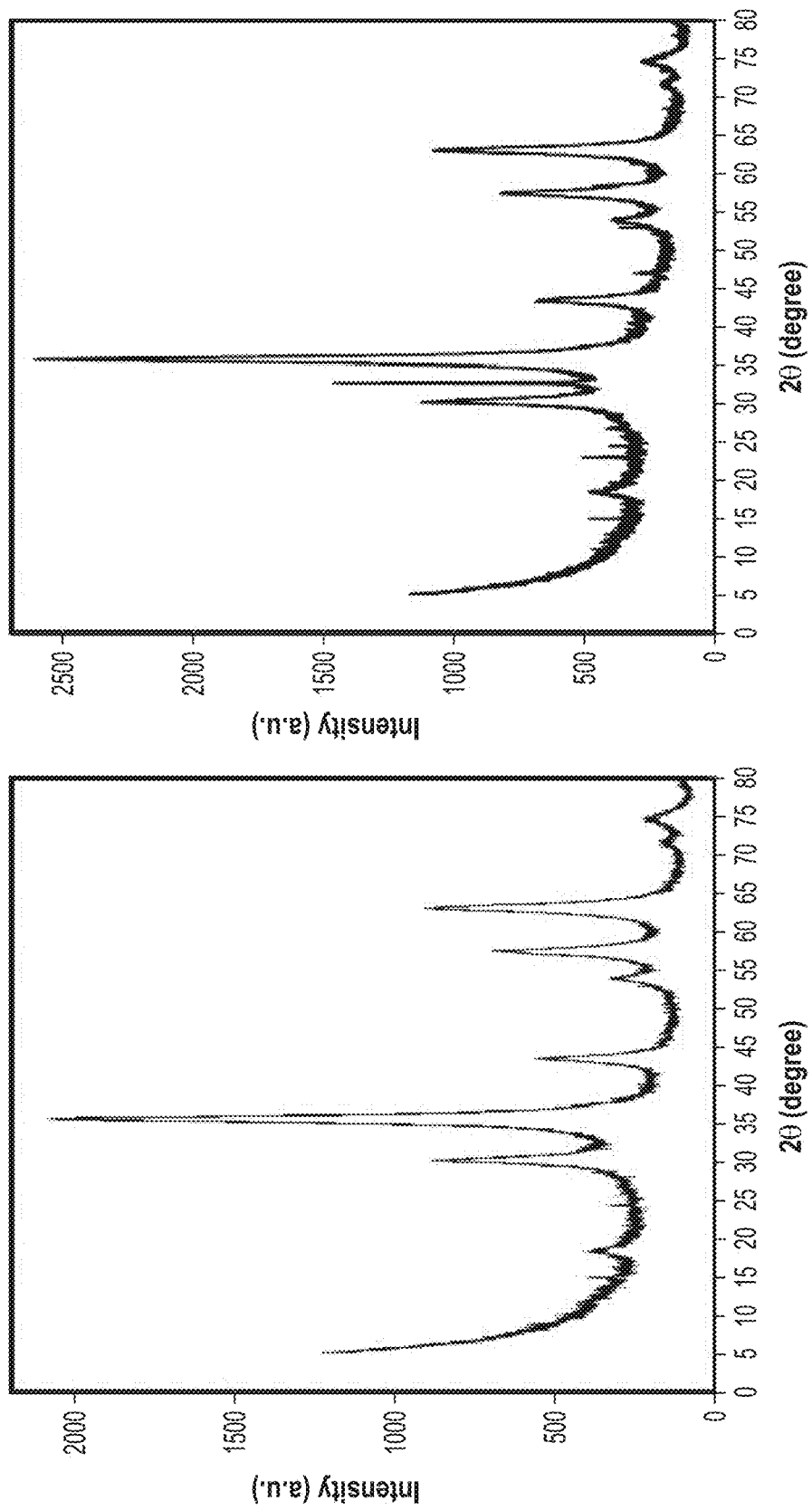

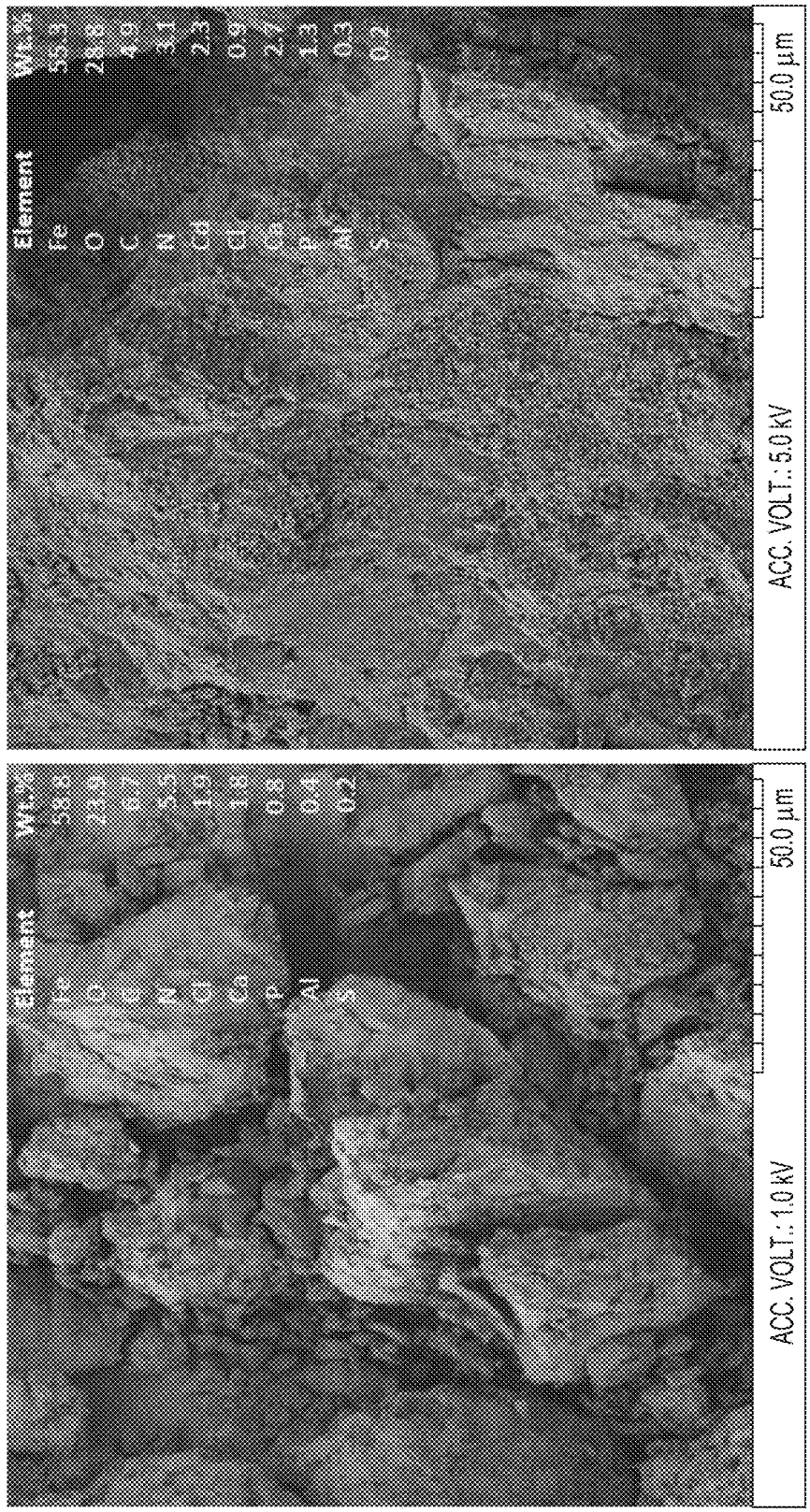

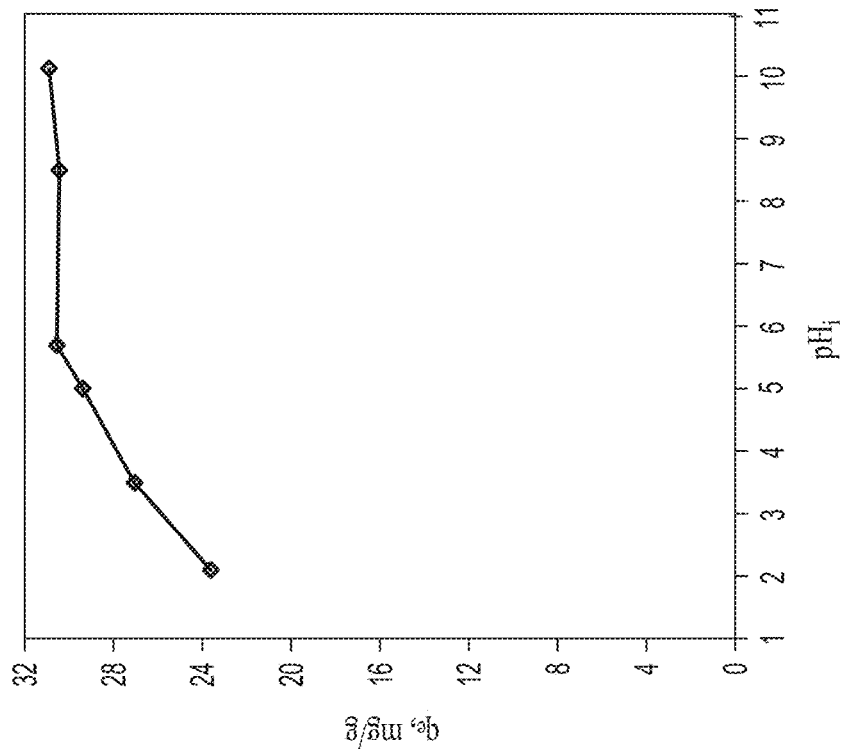
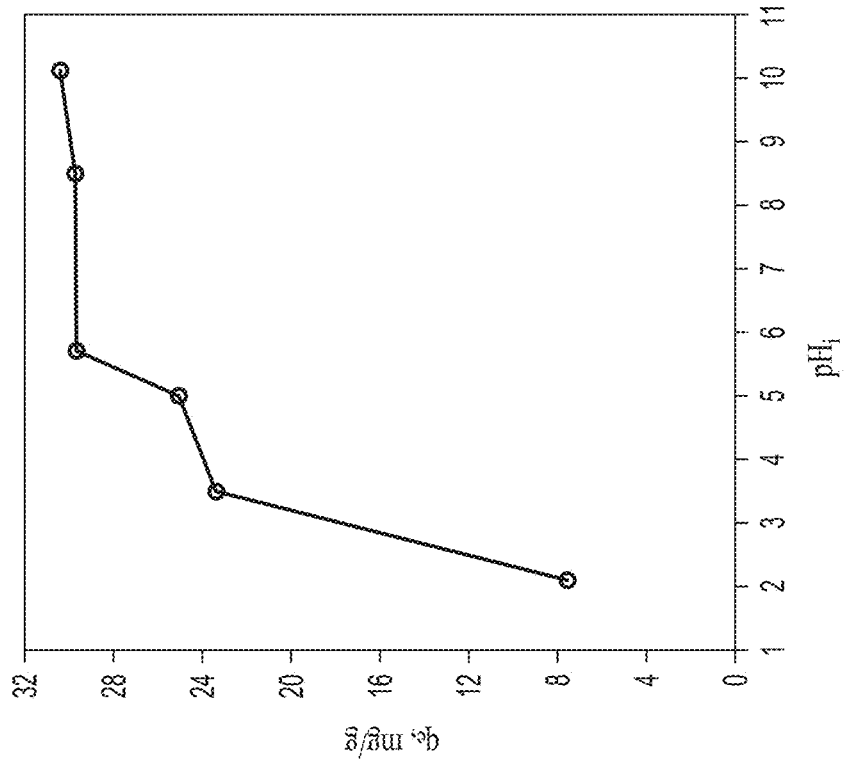
FIG. 8A
FIG. 8B

MAGNETIC HYDROCHAR SYNTHESIZED FROM MICROALGAL BIOMASS

BACKGROUND

1. Field

The disclosure of the present patent application relates to cadmium (Cd(II)) adsorption, and particularly to magnetic hydrochar synthesized from microalgal biomass for the adsorption of Cd(II).

2. Description of the Related Art

In general, Cd(II) is used to manufacture nickel-cadmium rechargeable batteries, metal plating, and rods in nuclear reactors to control atomic fission reaction. It is a soft, malleable, ductile, and bluish white metal with respective atomic number, atomic mass, and electronic configuration viz. 48, 112.4, and $[Kr] 4d^{10}5s^2$. It is considered a highly toxic non-essential heavy metal and is a suspected carcinogen. Acute toxicity can severely damage renal and reproductive systems, and red blood corpuscles. It can also cause hypertensive disorders. Therefore, it is essential to remove/reduce Cd(II) from waste effluents before their discharge to surface or subsurface water.

Adsorption is a commonly used process to sequester heavy metals from water. Technical feasibility, economic ease, and effectiveness at very low adsorbate concentration are some of the major merits of adsorption process. A wide range of synthetic and non-synthetic adsorbents have been used for water treatment.

Microalgae have recently gained considerable attention as potential clean energy sources. Microalgae benefit from the capacity to capture renewable solar energy and offer the additional environmental benefit of $CO_2$ fixation. Further, the microalgal cell wall includes carboxylic, hydroxyl, amino, phosphate, and sulfhydryl groups that possess relatively high binding capacities for heavy metals ions.

Thus, magnetic hydrochar (mHC) synthesized from microalgal biomass for the adsorption of cadmium solving the aforementioned problems is desired.

SUMMARY

The magnetized hydrochar (mHC) synthesized from microalgal biomass may be synthesized by subjecting a microalgal biomass to a hydrothermal carbonization (HTC) reaction to produce hydrochar, chemically activating the hydrochar with hydrogen peroxide $H_2O_2$, and magnetizing the activated hydrochar through coprecipitation. The resulting mHC may be used to adsorb Cd(II) ions from an aqueous environment.

In an embodiment, the microalgal biomass may be any microalgal species that is readily available. The microalgal biomass may be waste microalgal biomass, such as waste biomass used in biofuel production. In an embodiment, the microalgal biomass used to generate the hydrochar may be selected from *Chlorella vulgaris* FR751187 and *Scenedesmus obliquus* GU732418.

In an embodiment, the mHC may be used in water treatment to adsorb Cd(II) from an aqueous environment. In a further embodiment, the mHC may be used to adsorb Cd(II) from waste effluent before it is discharged into surface or subsurface water.

These and other features of the present subject matter will become readily apparent upon further review of the following specification.

BRIEF DESCRIPTION OF THE DRAWINGS

FIG. 1A depicts a graph illustrating nitrogen adsorption/desorption isotherms of mCVHC.

FIG. 1B depicts a graph illustrating nitrogen adsorption/desorption isotherms of mSOHC.

FIG. 2A depicts an X-ray diffraction spectrum of mCVHC.

FIG. 2B shows an X-ray diffraction spectrum of mSOHC.

FIG. 3A depicts a scanning electron micrograph of mCVHC.

FIG. 3B depicts a scanning electron micrograph of Cd(II) saturated mCVHC.

FIG. 8A depicts a graph illustrating the effect of pH on Cd(II) adsorption onto mCVHC.

FIG. 8B depicts a graph illustrating the effect of pH on Cd(II) adsorption onto mSOHC.

Similar reference characters denote corresponding features consistently throughout the attached drawings.

DETAILED DESCRIPTION OF THE PREFERRED EMBODIMENTS

Figures 4A, 4B:
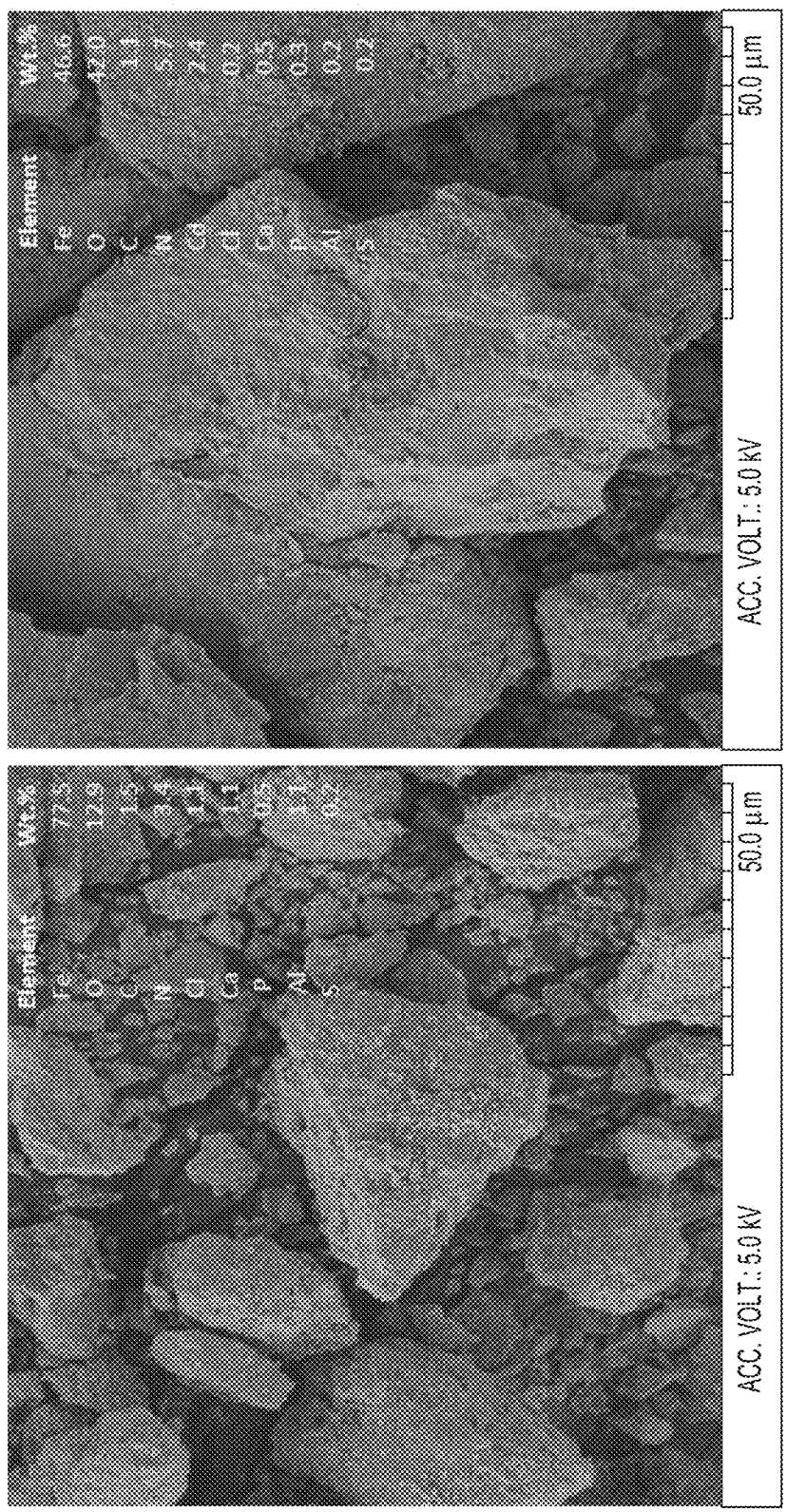
FIG. 4A depicts a scanning electron micrograph of mSOHC.
FIG. 4B depicts a scanning electron micrograph of Cd(II) saturated mSOHC.

The magnetized hydrochar (mHC) synthesized from microalgal biomass may be synthesized by subjecting a microalgal biomass to a hydrothermal carbonization (HTC) reaction to produce hydrochar, chemically activating the hydrochar with $H_2O_2$, and magnetizing the activated hydrochar through coprecipitation. The resulting mHC may be used to adsorb Cd(II) ions from an aqueous environment.

As used herein, "Hydrothermal Carbonization" (HTC), also known as wet torrefaction, hydrothermal (pre) treatment, or hot compressed water (pre)treatment is a technique used to generate carbonaceous hydrochar. HTC converts a raw biomass into hydrochar, which is characterized by its high carbon content and high calorific value. The use of HTC allows the treatment of a substrate with a moisture content of up to 75%-90% without requiring a drying pre-treatment step. HTC is performed in a high-pressure vessel by applying relatively high temperature and pressure to a biomass in liquid water for a few hours in the absence of air. The HTC is an exothermic process, may operate between 150 and 350° C. under autogenous pressure conditions for 0.5-8.0 hours. During HTC, the biomass undergoes dehydration, decarboxylation and decarbonylation.

In an embodiment, HTC may be performed on a microalgal biomass at 200° C. for 4 hours. The resulting hydrochar may be chemically activated by treatment with 10% $H_2O_2$ (v/v) solution. Further, the chemically activated hydrochar may be magnetized using coprecipitation.

In an embodiment, the hydrochar may be magnetized by coprecipitation with at least one source of metal ions. In a further embodiment, the hydrochar may be magnetized by coprecipitation with at least one source of iron, such a ferric chloride or ferrous chloride. This co-precipitation step may be performed using any known technique allowing for co-precipitation of hydrochar and at least one magnetic metal.

In an embodiment, the microalgal biomass may be any microalgal species that is readily available. The microalgal biomass may be waste microalgal biomass, such as waste biomass used in biofuel production. In an embodiment, the microalgal biomass used to generate the hydrochar may be selected from Chlorella vulgaris FR751187 or Scenedesmus obliquus GU732418.

In an embodiment, the mHC may be used in water treatment to adsorb Cd(II) from an aqueous environment. In a further embodiment, the mHC may be used to adsorb Cd(II) from waste effluent before it is discharged into surface or subsurface water.

In an embodiment, the mHC may be synthesized by subjecting *Chlorella vulgaris* FR751187 and *Scenedesmus obliquus* GU732418 microalgal biomass to a HTC reaction for about 4 hours under autogenous pressure condition at about 200° C. The developed *Chlorella vulgaris* hydrochar (CVHC) and *Scenedesmus obliquus* hydrochar (SOHC) samples may be chemically activated with $H_2O_2$. The chemically activated CVHC and SOHC samples may then be magnetized through co-precipitation to develop magnetized CVHC (mCVHC) and magnetized SOHC (mSOHC). The mCVHC and mSOHC samples developed according to this method may adsorb Cd(II) ions from an aqueous environment.

The following examples illustrate the present teachings.

EXAMPLE 1

Hydrochar Synthesis

*Chlorella vulgaris* FR751187 and *Scenedesmus obliquus* GU732418 species were isolated from freshwater in Wonju, Republic of Korea. These microalgal species were selected for adsorption experiments based on their disparate morphological characteristics and applications. *S. obliquus* GU732418 is ellipsoidal with appendages, lives in 2-, 4-, or 8-celled colonies, its diameter is 6 μm, surface area is 200 μm², and biovolume is 13 μm³. In contrast, *C. vulgaris* FR751187 is spherical without any appendages, lives as a single cell, has a diameter of 3.5 μm, a surface area of 154 m², and a biovolume of 23 μm³. These microalgal species have been reported to be promising candidates for biofuel production and, more importantly, can tolerate wastewater toxicity.

The selected microalgae were grown in four rectangular, vertical flat-plate photobioreactors (PBRs) (650×600×200 mm) constructed using transparent poly acrylic plastic material, with a total volume of 60 L each. Each PBR was loaded with 40 L of Bold's Basal Medium (BBM). A red light-emitting diode (LED) strip was attached on the outer wall of the PBRs to enhance microalgae growth. The PBRs were located indoors, where the temperature was maintained at about 25° C. under continuous illumination by red fluorescent light for 30 days. The cultures were continuously mixed by sparging with 0.2-μm filter sterilized air using an air pump (Toshipump Co., Ltd, Japan).

The cultures (80 ml) were consecutively transferred to an HTC reactor with a 200 ml volume and a polytetrafluoroethylene tube lining. The HTC reaction was carried out at 200° C. for 4 hours under autogenous pressure conditions. The resulting *C. vulgaris* FR751187 hydrochar (CVHC) and *S. obliquus* GU732418 hydrochar (SOHC) were washed with deionized water and dried overnight in an oven at 80° C. The dried CVHC and SOHC were manually crushed using a mortar and pestle and sieved to a uniform particle size. A gram of each of the CVHC and SOHC samples were chemically aged for 4 hours in 100 ml 10% $H_2O_2$ (v/v) solution over a magnetic stirrer at 100 rpm. Finally, the chemically aged CVHC and SOHC samples were magnetized using a co-precipitation process to develop magnetized CVHC (mCVHC) and magnetized SOHC (mSOHC). Briefly, a gram of chemically aged CVHC/SOHC was mechanically dispersed in 100 ml of deionized water. Ferric chloride hexahydrate [$FeCl_3 \cdot 6H_2O$, 2.36 g] and ferrous chloride tetrahydrate [$FeCl_2 \cdot 4H_2O$, 1.18 g] in a 2:1 molar ratio was added to the dispersion under continuous mechanical stirring at 100 rpm for 30 min. Nitrogen gas was continuously purged into the suspension to restrict iron oxidation during stirring. Drops of 40 ml ammonia solution were slowly added to the suspension under high speed mechanical stirring (1100 rpm). Finally, a black color hybrid, the mCVHC or mSOHC, respectively, was precipitated, separated by applying an external magnetic field, washed with deionized water to neutral pH, and finally washed with ethyl alcohol.

EXAMPLE 2

Analysis of Magnetized Hydrochar

Samples of mCVHC and mSOHC synthesized according to Example 1 were separated into two groups for analysis. One set of samples of mCVHC and mSOHC remained pristine, while a second set of samples of mCVHC and mSOHC were allowed to adsorb an excess of Cd(II) to obtain Cd(II) saturated mCVHC and mSOHC, respectively. The pristine mCVHC and mSOHC samples and the Cd(II) saturated mCVHC and mSOHC samples were then subjected to further analysis, as detailed below.

Type IV nitrogen adsorption/desorption isotherms (associated with mesoporous materials) with H2(b) type hysteresis loops were observed for both mCVHC (FIG. 1A) and mSOHC (FIG. 1B). The H2(b) type hysteresis loop is associated with pore blockage; however, the size distribution of neck widths is much larger. Generally, this is a characteristic loop observed for mesocellular silica foams and hydrothermally treated mesoporous ordered silica. The mCVHC and mSOHC samples were mesoporous with respective BET specific surface areas of 92.3 and 48.2 m²/g. For mCVHC, the observed BET, Langmuir, t-plot surface areas were 92.3, 205.3, and 131.6 m²/g, respectively. The observed BJH cumulative pore volume, and average pore diameter were 0.133 cm³/g and 35.3 Å, respectively. For mSOHC, the observed BET, Langmuir, t-plot surface areas were 48.2, 108.9, and 72.3 m²/g, respectively. The observed BJH cumulative pore volume, and average pore diameter were 0.100 cm³/g and 45.8 Å, respectively.

The X-ray diffraction (XRD) patterns of the mCVHC and mSOHC samples displayed sharp peaks with 8.3 and 8.6 nm as their respective crystallite sizes. (See FIGS. 2A-2B) A low intensity 2θ diffraction peak at ~14.9° (characteristic of cellulose) was observed in both the mCVHC and mSOHC XRD patterns. The 2θ diffraction peaks at 30.1°, 35.5°, 43.2°, 54.0°, 57.3°, and 62.7° were common in both mCVHC and mSOHC XRD patterns, well matched with cubic structure similar to magnetite ($Fe_3O_4$) (ICSD Card No. 01-076-9718). The crystallite sizes (D) of both mCVHC and mSOHC were determined from their respective XRD patterns by employing Debye-Scherrer's equation:

$$D(nm) = K \times \frac{\lambda}{(\beta \cos\theta)}$$

wherein K is a Scherrer's constant that depends on crystallites morphology, θ is the Bragg's peak, λ is the X-ray wavelength, and β is full width at half maximum of XRD peak. The magnitudes of D for mCVHC and mSOHC were 8.3 and 8.6 nm, respectively.

Morphological analysis of mCVHC using scanning electron microscopy (SEM) demonstrated that the mCVHC surface was porous with rough and uneven patches of non-uniform size and irregular geometry. (See FIG. 3A) An elemental analysis showed that the mCVHC surface was elementally enriched with a large amount of Fe (expected due to magnetization), along with O, C, N, and Cl, Ca and traces of P, Al, and S. After Cd(II) adsorption, the pores over the mCVHC surface were well occupied with Cd(II) ions confirmed through elemental analysis of Cd(II) saturated mCVHC. (See FIG. 3B) SEM analysis of mSOHC revealed a porous surface with sharp edged particles of non-uniform size. (See FIG. 4A) Elemental analysis showed the presence of large amounts of Fe, along with O, C, N, Cl, Ca, and traces of P and S. After Cd(II) adsorption, the porosity of mSOHC surface decreases, while the size of particles present over its surface due to the deposition of Cd(II) ions increases, confirmed by appearance of Cd during elemental analysis. (See FIG. 4B)

Figure 5:
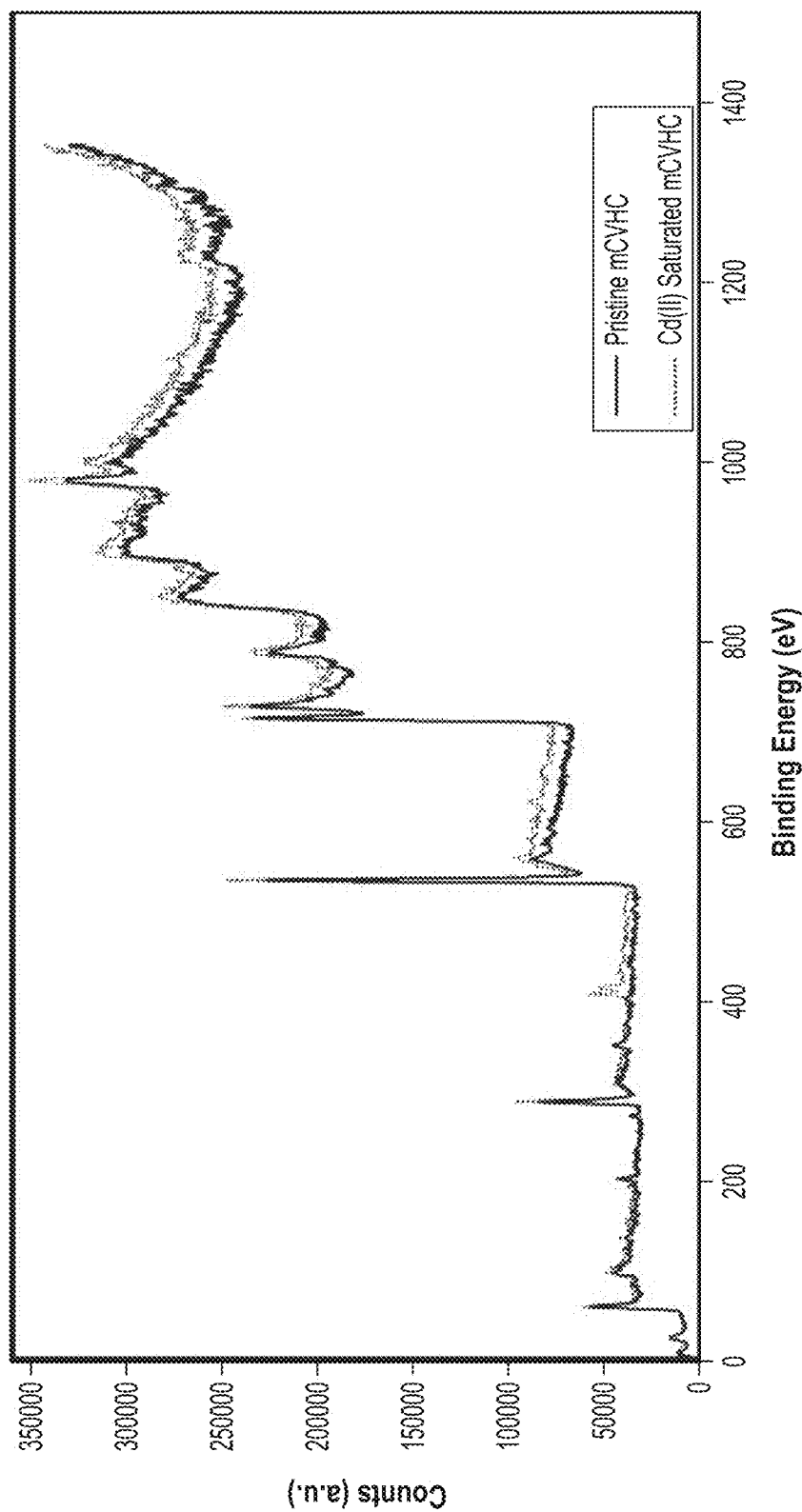
FIG. 5 depicts an X-ray photoelectron survey plot of mCVHC and Cd(II) saturated mCVHC.
Figure 6:
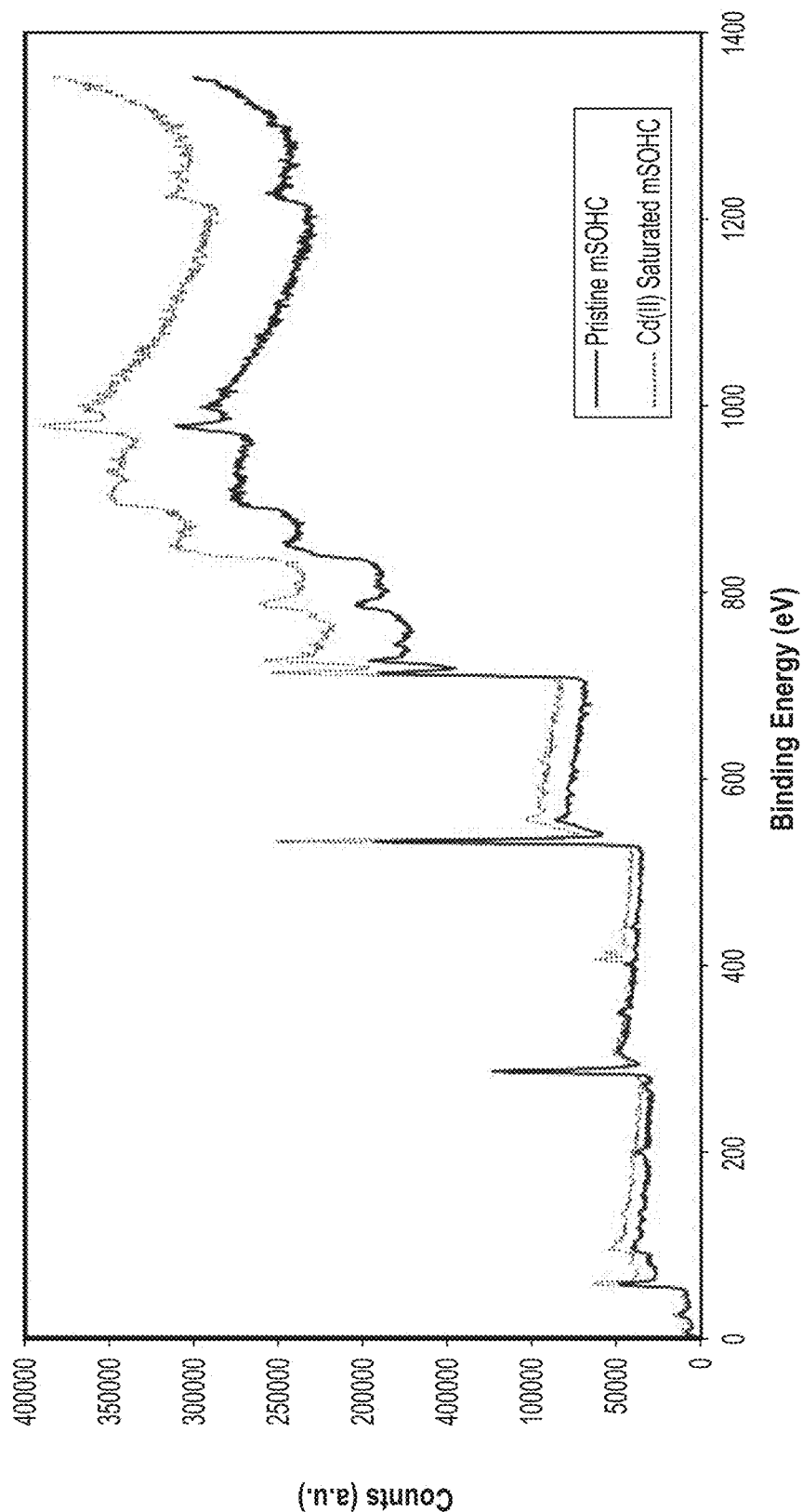
FIG. 6 depicts an X-ray photoelectron survey plot of mSOHC and Cd(II) saturated mSOHC.

X-ray photoelectron spectroscopy (XPS) analysis of the mCVHC and mSOHC samples showed major peaks for C1s, O1s, and Fe2p at binding energies ~284.9, ~530.4, and 711.1 eV, respectively. (See FIGS. 5-6) After Cd(II) adsorption, Cd(II) saturated mCVHC and Cd(II) saturated mSOHC samples' XPS spectra showed a new peak at ~405.6 eV for Cd3d. X-ray photoelectron spectroscopic (XPS) analysis of the mCVHC found peaks for C1s, O1s, Fe2p, Cl2p, Ca2p, and N1s at binding energies of 284.8, 530.31, 711.06, 198.58, 354.32, and 400.2 eV (See FIG. 5). After Cd(II) adsorption, a new peak for Cd3d arose at 405.47 eV binding energy, confirming Cd(II) adsorption over the mCVHC surface. XPS analysis of mSOCH found peaks for C1s, O1s, Fe2p, Cl2p, Ca2p, and N1s at binding energies of 284.96, 530.37, 711.04, 198.47, 347.43, and 400.2 eV (See FIG. 6). After Cd(II) adsorption, a new peak for Cd3d arose at 405.68 eV binding energy, confirming adsorption over the mSOHC surface.

Figure 7B:
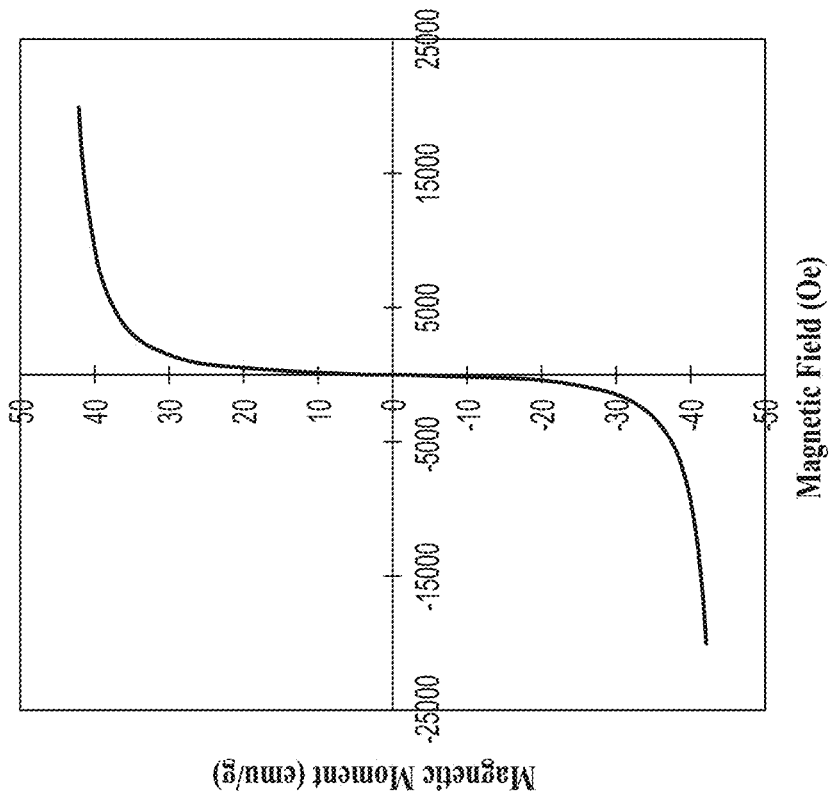
FIG. 7B depicts a vibrating sample magnetometer (VSM) analysis plot of mSOHC.
Figure 7A:
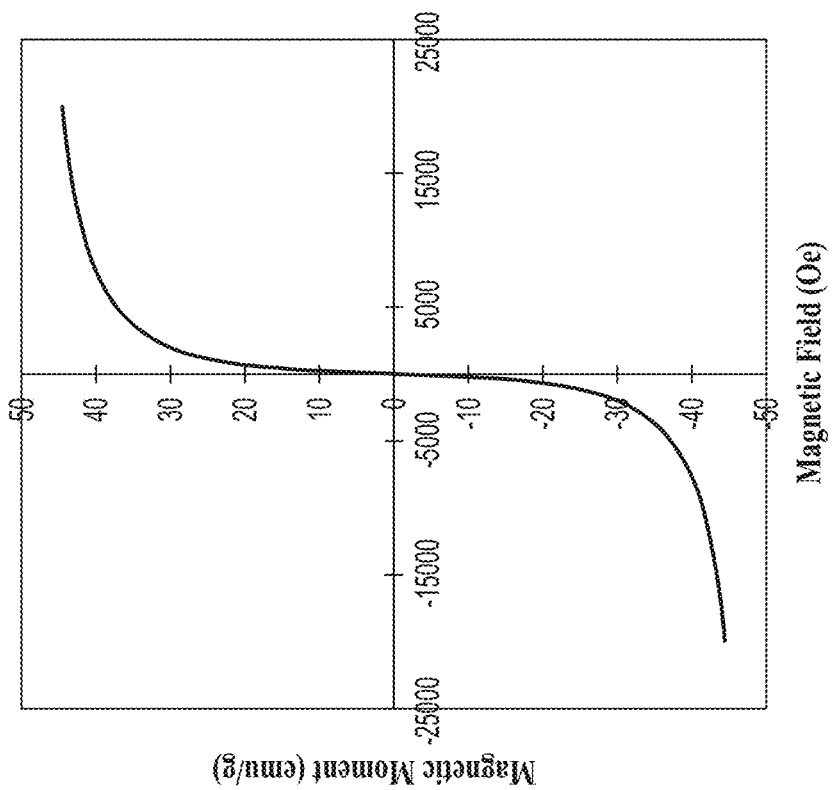
FIG. 7A depicts a vibrating sample magnetometer (VSM) analysis plot of mCVHC.

Vibrating sample magnetometer (VSM) analysis showed superparamagnetic behavior for both mCVHC and mSOHC, with their respective saturation magnetization magnitudes of 44.3 and 42.0 emu/g. The VSM analysis was carried out by applying an external magnetic field of 20000 Oe at about 300 K. S-shaped curves between magnetization and applied field (VSM plots) without hysteresis were observed for both mCVHC (FIG. 7A) and mSOHC (FIG. 7B). In addition, negligible coercivity and retentivity was found for both mCVHC and mSOHC, depicting their superparamagnetic behavior.

EXAMPLE 3

Adsorption Studies of Magnetized Hydrochar

Batch mode adsorption experiments were carried out in 100 ml Erlenmeyer flasks to study aqueous phase Cd(II) adsorption onto mCVHC and mSOHC. Cd(II) solutions (25 ml of initial concentrations ($C_o$): 25 mg/l) were equilibrated separately with 0.02 g of mCVHC and 0.02 g of mSOHC over a temperature controlled water bath shaker at 100 rpm for 24 hr. At equilibrium, mCVHC and mSOHC were magnetically separated from Cd(II) solutions and residual Cd(II) concentrations (i.e. concentrations at equilibrium, $C_e$) were quantitatively analyzed by atomic absorption spectrometer (AAS: Perkin Elmer, PinAAcleTM 900T). The amounts of Cd(II) adsorbed on mCVHC and mSOHC were calculated as:

$$\text{Adsorption capacity at equilibrium}(q_e) = (C_o - C_e) \times \frac{V}{m}$$

wherein $q_e$ (mg/g) is the adsorption capacity at equilibrium, $C_o$ and $C_e$ (mg/L) are the initial and equilibrium concentrations of adsorbate, V (L) is the volume of adsorbate, and m (g) is the mass of adsorbent. The effect of varying numerous experimental parameters viz., adsorbate solution pH, contact time, adsorbate concentration, and reaction temperature on adsorption was evaluated.

The adsorption of Cd(II) ($C_o$: 25 mg/L) on mCVHC as a function of initial pH (pHi) was studied for pHi range: 2-10 (See FIG. 8A). At pHi: 2.1, very low (7.6 mg/g) Cd(II) uptake was observed, sharply increased to 23.4 mg/g at pHi: 3.5. A slow increase in Cd(II) adsorption (from 23.4 to 29.7 mg/g) was observed between pHi: 3.5 and 5.7 gradually reaching 30.4 mg/g at pHi: 10.1.

The adsorption of Cd(II) ($C_o$: 25 mg/L) on mSOHC as a function of pHi was studied for pHi range: 2-10. Comparatively better Cd(II) uptake (23.6 mg/g) than mCVHC was observed at pHi: 2.1, slowly reached to 30.5 mg/g at pHi: 5.7, and thereafter gradually to 30.9 mg/g at pHi: 10.1 (See FIG. 8B).

Figure 9A:
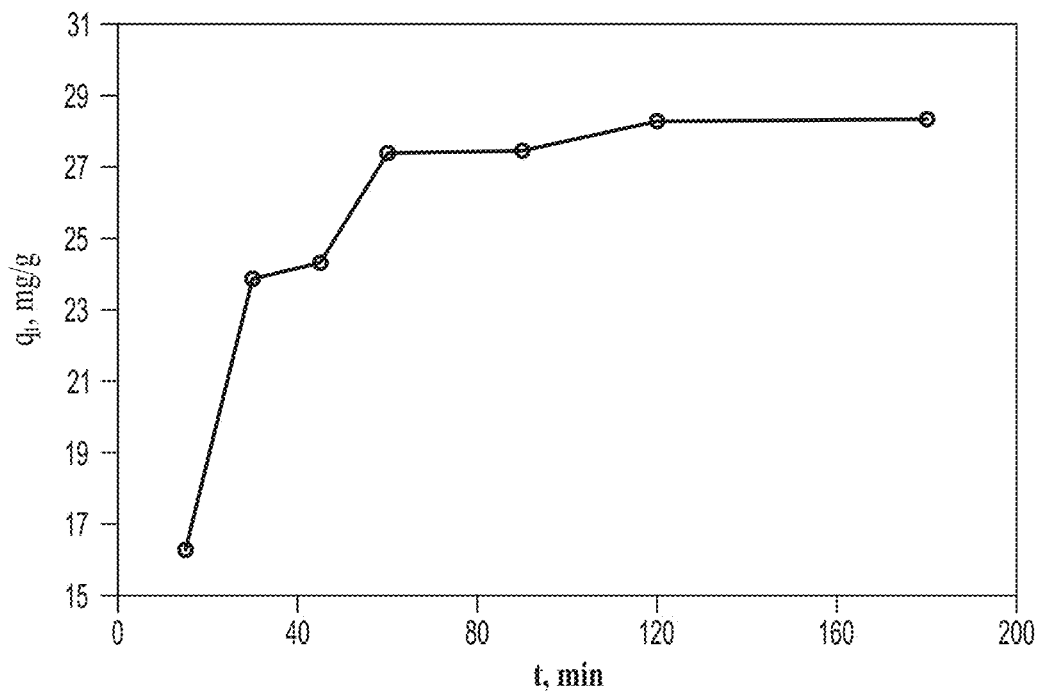
FIG. 9A depicts a graph illustrating a contact time plot for Cd(II) adsorption onto mCVHC.

The adsorption of Cd(II) at $C_o$: 25 mg/L as a function of contact time on mCVHC was studied and is illustrated in FIG. 9A. The adsorption of Cd(II) after 15 min contact time was 16.2 mg/g, increased to 27.4 mg/g in 60 min, and reached to 28.3 mg/g at equilibrium in 120 min.

Figure 9B:
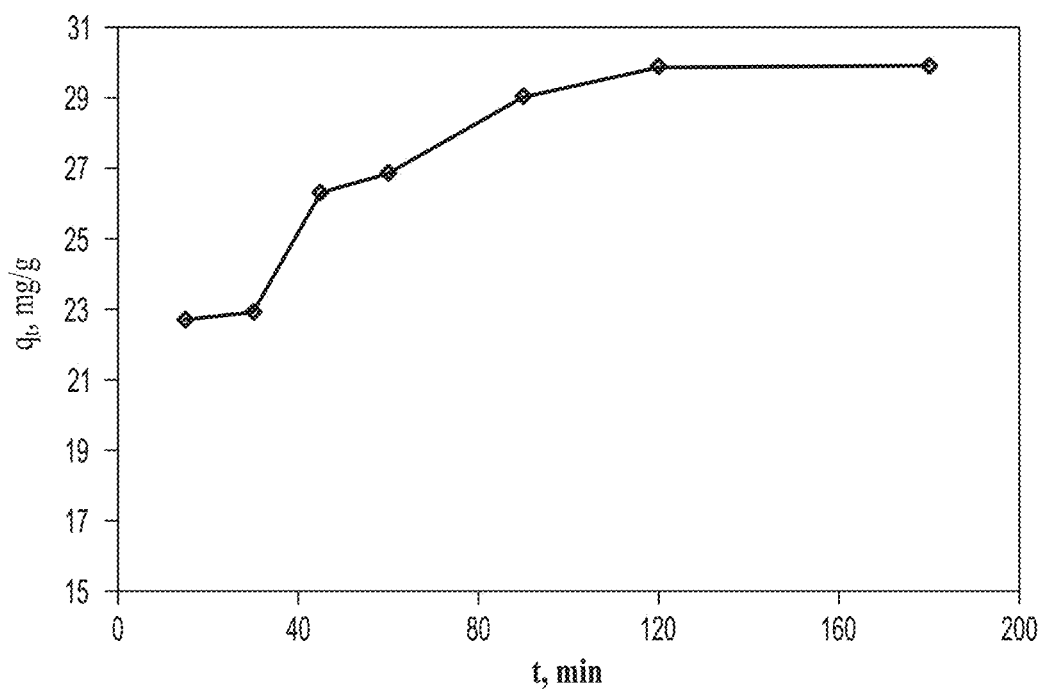
FIG. 9B depicts a graph illustrating a contact time plot for Cd(II) adsorption onto mSOHC.

The adsorption of Cd(II) at $C_o$: 25 mg/L as a function of contact time on mSOHC was studied and is illustrated in FIG. 9B. Very slow increase in Cd(II) adsorption (from 22.7 to 22.9 mg/g) was observed between 15 and 30 min, reaching 29 mg/g in 90 min, attaining equilibrium in 120 min with 29.9 mg/g Cd(II) uptake.

Figure 10A:
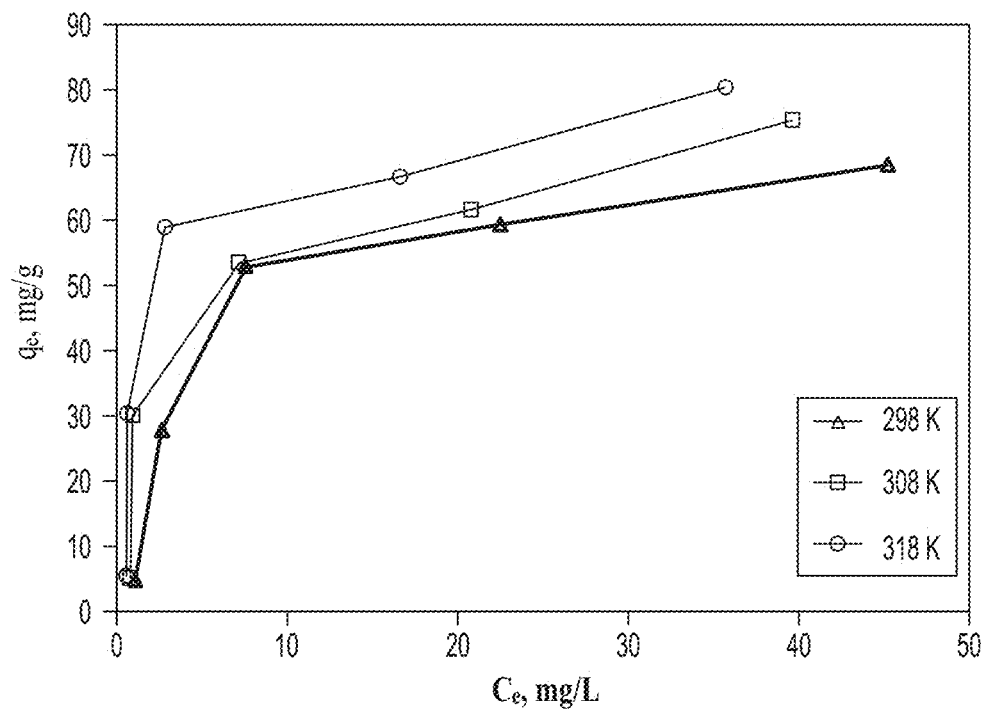
FIG. 10A depicts a graph illustrating the effect of initial concentration on Cd(II) adsorption at varied temperature onto mCVHC.

The adsorption of Cd(II) on mCVHC was studied by varying $C_o$ range: 5-100 mg/L at different temperatures (T: 298-318 K). For the studied $C_o$ range, the adsorption of Cd(II) at 298 K varied between 4.9 and 68.5 mg/g, at 308 K varied between 5.1 and 75.4 mg/g, and at 318 K varied between 5.5 and 80.4 mg/g (See FIG. 10A).

Figure 10B:
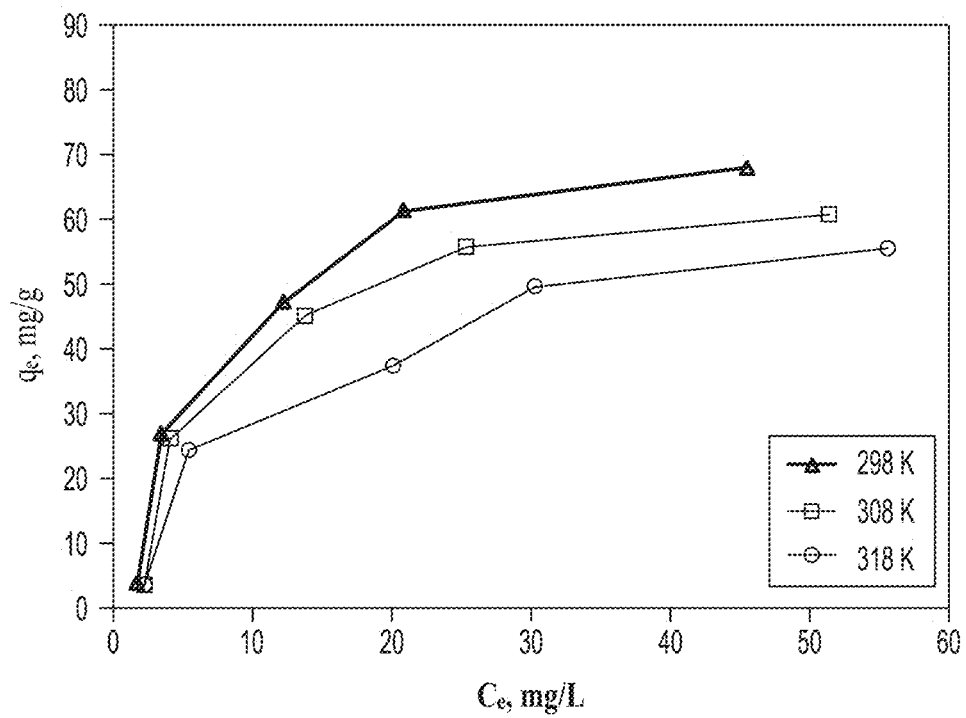
FIG. 10B plot depicts a graph illustrating the effect of initial concentration on Cd(II) adsorption at varied temperature onto mSOHC.

The adsorption of Cd(II) on mSOHC was studied by varying Co range: 5-100 mg/L at different temperatures (T: 298-318 K). For the studied $C_o$ range, the adsorption of Cd(II) at 298 K varied between 4 and 68.1 mg/g, at 308 K varied between 3.5 and 60.7 mg/g, and at 318 K varied between 3.3 and 55.5 mg/g (See FIG. 10B).

Langmuir and Freundlich isotherm models in linearized forms were fitted to Cd(II) adsorption data on mCVHC and mSOHC, expressed as:

$$\frac{C_e}{q_e} = \frac{1}{K_L q_m} + \frac{1}{q_m} \times C_e$$

$$\log q_e = \log K_F + \frac{1}{n} \log C_e$$

wherein $K_L$ (L/mg) and $K_F$ ((mg/g) (L/mg)$^{1/n}$) are Langmuir constant related to heat of adsorption and Freundlich constant related to bonding energy, respectively, $q_m$ (mg/g) is the maximum monolayer adsorption capacity, and n is a Freundlich constant related to deviation in adsorption from linearity.

Tables 1-2 present isotherm parameters for Cd(II) adsorption at varied temperatures on mCVHC and mSOHC, respectively. Comparatively higher regression coefficient ($R^2$) values supported fitting of Langmuir isotherm model to Cd(II) adsorption data on mCVHC and mSOHC. The applicability of Langmuir isotherm model hinting towards monolayer Cd(II) coverage over mCVHC and mSOHC surfaces during adsorption. The magnitude of $K_L$ for Cd(II) adsorption on mCVHC increases with increase in temperature implying greater affinity of Cd(II) ions towards mCVHC surface, while reverse Cd(II) adsorption trend was observed on mSOHC. The $R_L$ values were ranged between 0 and 1 showing favorable adsorption process.

TABLE 1

Isotherm Model Parameters for the Adsorption of Cd(II) on mCVHC

| Temperature (K) | Langmuir isotherm | | | | Freundlich isotherm | | |
|---|---|---|---|---|---|---|---|
| | $q_m$ (mg/g) | $K_L$ (L/mg) | $R_L$ | $R^2$ | $K_F$ (mg/g)(L/mg)$^{1/n}$ | n | $R^2$ |
| 298 | 106.4 | 0.042 | 0.827 | 0.9874 | 6.92 | 1.43 | 0.8429 |
| 308 | 114.9 | 0.053 | 0.487 | 0.9835 | 8.69 | 1.49 | 0.8631 |
| 318 | 131.6 | 0.073 | 0.407 | 0.9870 | 12.5 | 1.62 | 0.8154 |

TABLE 2

Isotherm Model Parameters for the Adsorption of Cd(II) on mSOHC

| Temperature (K) | Langmuir isotherm | | | | Freundlich isotherm | | |
|---|---|---|---|---|---|---|---|
| | $q_m$ (mg/g) | $K_L$ (L/mg) | $R_L$ | $R^2$ | $K_F$ (mg/g)(L/mg)$^{1/n}$ | n | $R^2$ |
| 298 | 90.9 | 0.050 | 0.499 | 0.9830 | 6.56 | 1.42 | 0.8980 |
| 308 | 76.9 | 0.022 | 0.694 | 0.9776 | 2.79 | 1.11 | 0.8790 |
| 318 | 66.7 | 0.021 | 0.701 | 0.9820 | 2.03 | 1.15 | 0.9350 |

Pseudo-first-order and pseudo-second-order kinetic models were applied to Cd(II) ($C_o$: 25 mg/L) adsorption data on mCVHC and mSOHC, expressed as:

$$\log(q_{e1} - q_t) = \log q_{e1} - \frac{k_1}{2.303} \times t$$

$$\frac{t}{q_t} = \frac{1}{k_2 q_{e2}^2} + \frac{1}{q_{e2}} \times t$$

wherein $q_{e1}$ (mg/g), $q_{e2}$ (mg/g), and $q_t$ (mg/g) are the adsorption capacities for pseudo-first-order, pseudo-second-order models at equilibriums and at any time t, respectively, and wherein $k_1$ (1/min) and $k_2$ (g/mg-min) are the respective pseudo-first-order, and pseudo-second-order rate constants. Tables 3-4 present kinetic model parameters for Cd(II) adsorption on mCVHC and mSOHC. Comparatively higher $R^2$ values supported the fitting of pseudo-second-order model to kinetic data, further confirmed by nearer $q_{e2}$ and $q_{e,exp}$ values.

TABLE 3

Kinetic Model Parameters for the Adsorption of Cd(II) on mCVHC

| $C_o$ (mg/L) | $q_{e,exp}$ (mg/g) | Pseudo-first-order | | | Pseudo-second-order | | |
|---|---|---|---|---|---|---|---|
| | | $q_{e1}$ (mg/g) | $k_1$ (1/min) | $R^2$ | $q_{e2}$ (mg/g) | $k_2$ (g/mg-min) | $R^2$ |
| 25 | 28.27 | 23.27 | 0.0458 | 0.9237 | 30.12 | 0.0035 | 0.9983 |

TABLE 4

Kinetic Model Parameters for the Adsorption of Cd(II) on mSOHC

| | | Pseudo-first-order | | | Pseudo-second-order | | |
|---|---|---|---|---|---|---|---|
| $C_o$ (mg/L) | $q_{e,exp}$ (mg/g) | $q_{e1}$ (mg/g) | $k_1$ (1/min) | $R^2$ | $q_{e2}$ (mg/g) | $k_2$ (g/mg-min) | $R^2$ |
| 25 | 29.87 | 13.88 | 0.0292 | 0.9458 | 31.44 | 0.0037 | 0.9988 |

Thermodynamic parameters viz. standard enthalpy change ($\Delta H°$), standard entropy change ($\Delta S°$), and standard free energy change ($\Delta G°$) for Cd(II) adsorption on mCVHC and mSOHC at varied $C_o$ values were evaluated and calculated as:

$$\ln K_c = \frac{\Delta S°}{R} - \frac{\Delta H°}{R} \times \frac{1}{T}$$

$$\Delta G° = -RT \ln K_c$$

wherein R is a universal gas constant (8.314 J/mol-K), T is absolute temperature (K), $K_c$ is adsorption constant ($K_c = C_{Ae}/C_e$), $C_{Ae}$ is concentration of adsorbate on adsorbent, $C_e$ is residual concentration on adsorbate in aqueous phase.

The $\Delta H°$ magnitude for Cd(II) adsorption on mCVHC was endothermic (positive values) (Table 5), while on mSOCH was exothermic (negative values) (Table 6). The $\Delta S°$ magnitude for Cd(II) adsorption on mCVHC was positive reflecting its stronger affinity to adsorb Cd(II) ions from aqueous environment. A decrease in $\Delta S°$ magnitude with increase in adsorbate concentration showed a decrease in its adsorption affinity. Additionally, a positive $\Delta S°$ magnitude is indicative of randomness at solid/solution interface. Conversely, $\Delta S°$ magnitude for Cd(II) adsorption on mSOHC was negative reflecting its weaker affinity to adsorb Cd(II) ions. Also, it implies that the adsorption process is enthalpy driven. The $\Delta S°$ value for Cd(II) adsorption on mSOHC increases with increase in $C_o$ values, suggesting better Cd(II) adsorption affinity at higher concentration. The magnitude of $\Delta G°$ for Cd(II) adsorption on both mCVHC and mSOHC was negative, which is significant for adsorption.

TABLE 5

Thermodynamics Parameters for the Adsorption of Cd(II) on mCVHC

| $C_o$ | $\Delta H°$ | $\Delta S°$ | (−) $\Delta G°$ (kJ/mol) | | |
|---|---|---|---|---|---|
| (mg/L) | (kJ/mol) | (J/mol-K) | 298K | 308K | 318K |
| 25 | 26.16 | 100.29 | 3.64 | 4.88 | 5.63 |
| 50 | 29.54 | 112.57 | 4.26 | 4.55 | 6.55 |
| 100 | 15.63 | 54.12 | 0.475 | 1.07 | 1.55 |

TABLE 6

Thermodynamics Parameters for the Adsorption of Cd(II) on mSOHC

| $C_o$ | (−) $\Delta H°$ | (−) $\Delta S°$ | (−) $\Delta G°$ (kJ/mol) | | |
|---|---|---|---|---|---|
| (mg/L) | (kJ/mol) | (J/mol-K) | 298K | 308K | 318K |
| 25 | 39.54 | 119.48 | 4.12 | 2.36 | 1.75 |
| 50 | 34.98 | 107.25 | 2.78 | 2.46 | 0.607 |
| 100 | 15.97 | 52.17 | 0.44 | 0.145 | 0.596 |

EXAMPLE 4

Leaching and Regeneration Studies of Magnetized Hydrochar

During batch mode regeneration studies, 0.02 g of mCVHC and mSOHC samples were saturated with 25 mL Cd(II) solutions of $C_o$: 25 mg/L in a series of Erlenmeyer flasks. Afterwards, saturated samples were magnetically separated and residual Cd(II) concentration was qualitatively analyzed by AAS to estimate the Cd(II) ion concentration adsorbed over saturated mCVHC and mSOHC samples. The samples were washed with deionized water to remove unadsorbed Cd(II) ions traces. To elute Cd(II) ions, saturated mCVHC and mSOHC samples were treated with nitric acid ($HNO_3$), hydrochloric acid (HCl), and sulfuric acid ($H_2SO_4$) solutions of 0.01M concentrations. The amount of Cd(II) desorbed was calculated according to the equation:

$$\text{Desorption}(\%) = \frac{\text{Concentration of } Cd(II) \text{ ions desorbed}}{\text{Initial Concentration of } Cd(II) \text{ adsorbed}} \times 100$$

Figure 11A:
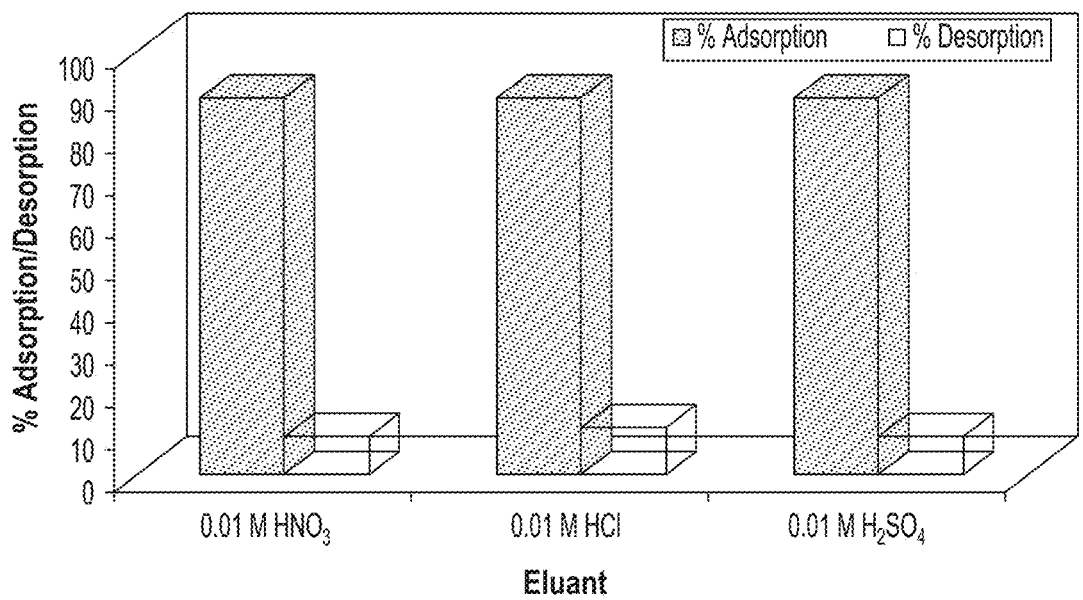
FIG. 11A depicts a graph illustrating recovery of Cd (II) from saturated mCVHC by various eluents.
Figure 11B:
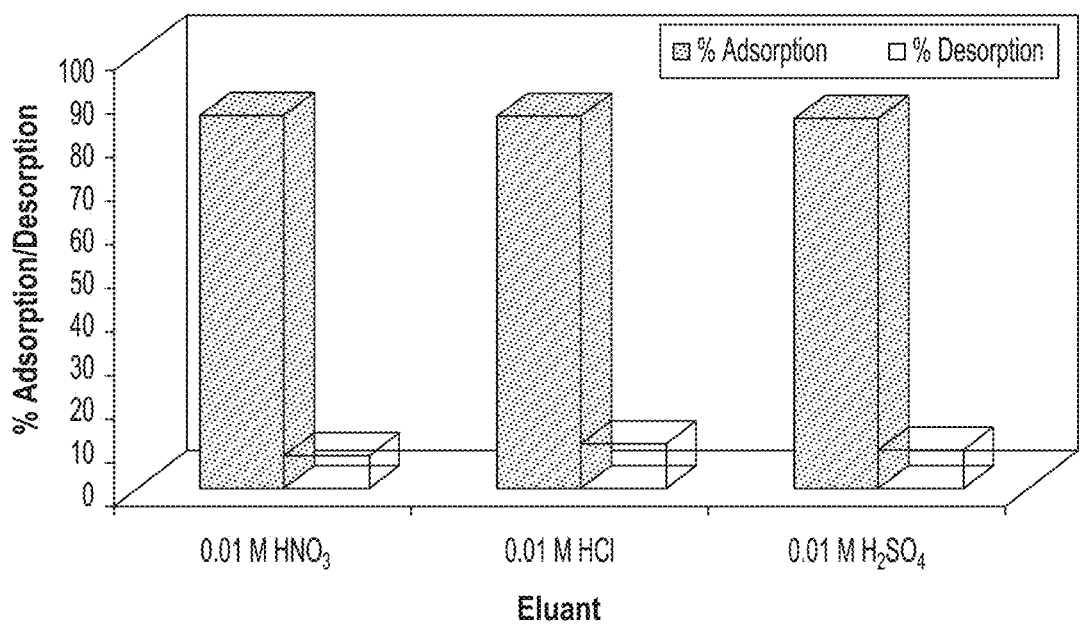
FIG. 11B depicts a graph illustrating recovery of Cd (II) from saturated mSOHC by various eluents.

The maximum amount (11.4%) of Cd(II) was desorbed by 0.01M HCl from mCVHC, followed by 0.01M $HNO_3 > 0.01M\ H_2SO_4$ (See FIG. 11A). On the other hand, Cd(II) elution from mSOHC was 10.7% (maximum) by 0.01 M HCl, followed by 0.01M $H2SO_4 > 0.01M\ HNO_3$ (See FIG. 11B).

Figure 12A:
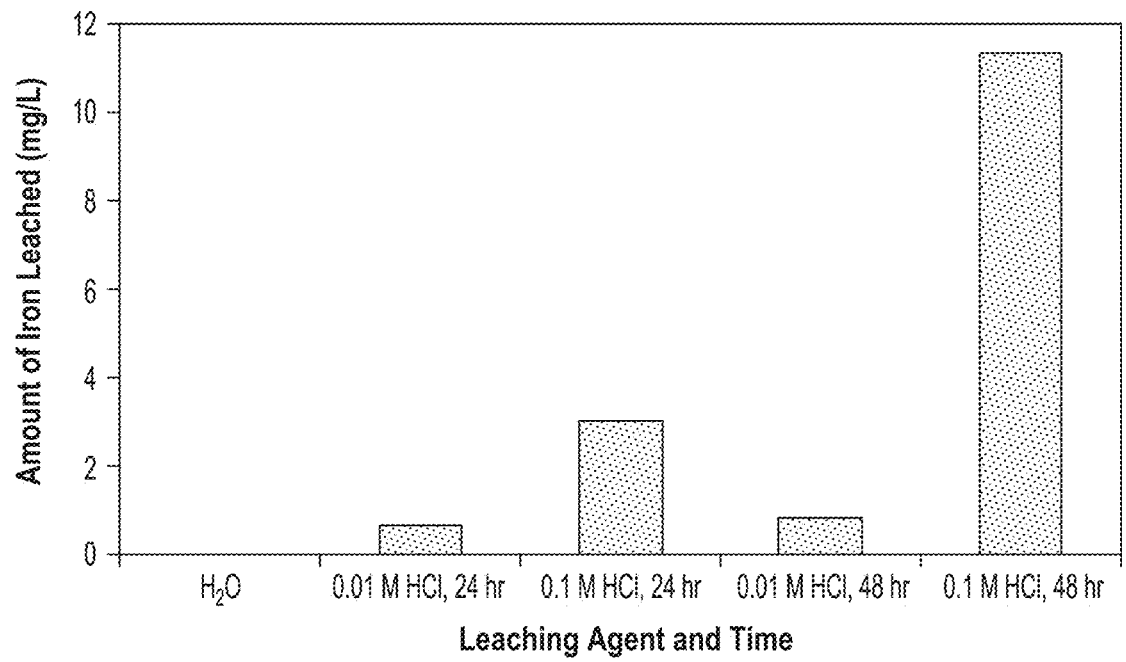
FIG. 12A depicts a graph illustrating iron leaching from mCVHC.
Figure 12B:
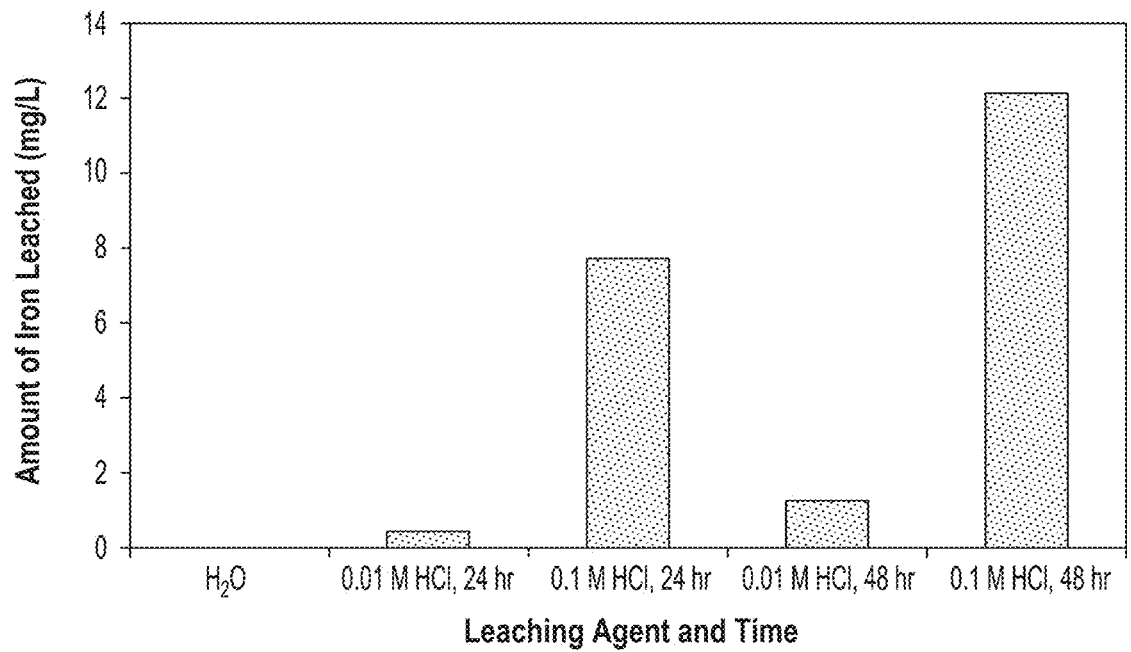
FIG. 12B depicts a graph illustrating iron leaching from mSOHC.

A study to test iron leaching from mCVHC and mSOHC samples by HCl (the eluent demonstrating the maximum Cd(II) recovery) was carried out by varying HCl concentration and contact time. As illustrated in FIG. 12A, iron leaching from mCVHC was not detectable in water (quantitatively tested by inductively coupled plasma-mass spectrometry, ICP-MS: Elmer, NexION 300D, USA). At 0.01M HCl concentration, 0.66mg/L of iron was leached after 24 hours, increased to 0.82 mg/L after 48 hours. At 0.1 M HCl concentration, 3 mg/L of iron was leached out within 24 hours. The leached amount increased to 11.3 mg/L after 48 hours. The iron was not leached from mSOHC by water (FIG. 12B). At 0.01 M HCl concentration, 0.39 and 1.22 mg/L of iron was leached out after 24 and 48 hours, respectively. At 0.1 M HCl concentration, after 24 and 48 hours the amount of iron leached was 7.68 and 12.09 mg/L, respectively.

It is to be understood that the magnetic hydrochar synthesized from microalgal biomass is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

The invention claimed is:

1. A hydrochar composition comprising magnetized hydrochar synthesized from a microalgal biomass; wherein the microalgal biomass comprises at least one of *Chlorella vulgaris* and *Scenedesmus obliquus*.

2. The hydrochar composition as recited in claim 1, wherein the microalgal biomass comprises *Chlorella vulgaris*.

3. The hydrochar composition as recited in claim 1, wherein the microalgal biomass comprises *Scenedesmus obliquus*.

4. A method of synthesizing magnetic hydrochar comprising:
   subjecting a microalgal biomass to hydrothermal carbonization to produce hydrochar;
   chemically activating the hydrochar with hydrogen peroxide to provide a chemically activated hydrochar; and
   magnetizing the chemically activated hydrochar using co-precipitation to obtain magnetized hydrochar;
   wherein
   the microalgal biomass comprises at least one of *Chlorella vulgaris* and *Scenedesmus obliquus*.

5. The method of synthesizing magnetic hydrochar as recited in claim 4, wherein microalgal biomass is subjected to hydrothermal carbonization in a hydrothermal carbonization reactor at about 200° C. for about 4 hours under autogenous pressure conditions.

6. The method of synthesizing magnetic hydrochar as recited in claim 4, wherein the microalgal biomass comprises *Chlorella vulgaris*.

7. The method of synthesizing magnetic hydrochar as recited in claim 4, wherein the microalgal biomass comprises *Scenedesmus obliquus*.

8. The method of synthesizing magnetic hydrochar as recited in claim 4, wherein the hydrochar is chemically activated with 10% hydrogen peroxide for 4 hours.

9. The method of synthesizing magnetic hydrochar as recited in claim 4, wherein the magnetized hydrochar is capable of adsorbing cadmium from an aqueous environment.

10. A method of water remediation comprising adsorbing cadmium from waste water by treating the waste water with magnetized hydrochar synthesized according to the method of claim 4.

* * * * *